US006939669B2

(12) United States Patent
Kikuchi et al.

(10) Patent No.: US 6,939,669 B2
(45) Date of Patent: Sep. 6, 2005

(54) EXPANSION OF HEMATOPOIETIC CELLS USING MIDKINE OR PLEIOTROPHIN

(75) Inventors: Makoto Kikuchi, Fukuoka (JP); Shinya Ikematsu, Kanagawa (JP); Munehiro Oda, Kanagawa (JP); Sadatoshi Sakuma, Kanagawa (JP); Takashi Muramatsu, Aichi (JP)

(73) Assignee: Meiji Dairies Corporation, Tokyo (JP)

( * ) Notice: Subject to any disclaimer, the term of this patent is extended or adjusted under 35 U.S.C. 154(b) by 516 days.

(21) Appl. No.: 10/071,039

(22) Filed: Feb. 8, 2002

(65) Prior Publication Data

US 2002/0132984 A1 Sep. 19, 2002

Related U.S. Application Data

(62) Division of application No. 09/214,569, filed as application No. PCT/JP97/02401 on Jul. 10, 1997, now Pat. No. 6,383,480.

(30) Foreign Application Priority Data

Jul. 10, 1996 (JP) .............................. 8-198531

(51) Int. Cl.$^7$ ........................ C12N 5/00; C07K 14/475; C07K 14/52
(52) U.S. Cl. ........................... 435/4; 435/325; 435/375; 435/377; 530/350; 530/351; 530/399
(58) Field of Search ........................... 435/4, 375, 377, 435/325; 530/399, 300, 350, 351

(56) References Cited

U.S. PATENT DOCUMENTS

| 4,868,119 A | | 9/1989 | Clark et al. ............... 435/240.2 |
| 5,061,620 A | * | 10/1991 | Tsukamoto et al. ......... 435/7.21 |
| 5,087,448 A | * | 2/1992 | Burstein .................... 424/85.2 |
| 5,087,570 A | * | 2/1992 | Weissman et al. ........ 430/240.1 |
| 5,399,493 A | * | 3/1995 | Emerson et al. ............. 435/456 |
| 5,409,825 A | * | 4/1995 | Hoffman et al. ............. 435/384 |
| 5,437,994 A | * | 8/1995 | Emerson et al. ............. 435/373 |
| 5,461,029 A | | 10/1995 | Backer et al. .................. 514/2 |
| 5,472,867 A | * | 12/1995 | Kanz et al. ............. 435/240.25 |

FOREIGN PATENT DOCUMENTS

| EP | 0473233 A1 | 3/1992 | |
| EP | 0535336 A3 | 4/1993 | |
| EP | 0535336 A2 | 4/1993 | |
| EP | 0 569 703 A2 | 11/1993 | .......... A61K/37/02 |
| WO | WO 92/06712 | 4/1992 | |
| WO | WO 95/09640 | * 4/1995 | |

OTHER PUBLICATIONS

Kojima et al. Midkine is a heat and acid labile stable polypeptide capable of enhancing plasminogen activator and neurite outgrowth extension. Biochem Biophys Res Comm 216(2): 574–581, 1995.*

Szilvassy, S. The Biology of Hematopoietic stem cells. Arch Med Res 34: 446–460, 2003.*

Brugger et al. Ex vivo expansion of enriched peripheral blood CD34+ progenitor cells by stem cell factor, interleukin–1(Beta), IL–6, IL–3, interferon (gamma), and erythropoietin. Blood 81(10): 2579–2584, 1993.*

Vadhan–Raj et al. In vivo biologic activities of recombinant human granulocyte–macrophage colony–stimulating factor. Annals NY Acad. Sciences 554:231–240, 1989.*

Kadomatsu et al., "cDNA Cloning and Sequencing of a New Gene Intensely Expressed in Early Differentiation Stages ... Embryogenesis," Biochem. Biophys. Res. Commun. 151(3):1312–1318, 1988.

Kubo et al., "Different responses of human marrow and circulating erythroid progenitors to stem cell factor, interleukin–3 and granulocyte/macrophage colony–stimulating factor," Int. J. Hematol. 58:153–162, 1993.

Lyman et al., "Cloning of the Human Homologue of the Murine flt3 Ligand: A Growth Factor for Early Hematopoietic Progenitor Cells," Blood 83(10):2795–2801, 1994.

Rauvala, "An 18–kd heparin–binding protein of developing brain that is distinct from fibroblast growth factors," EMBO J. 8(10):2933–2941, 1989.

Shiohara et al., "Synergism of Interferon–γ and Stem Cell Factor on the Development of Murine Hematopoietic Progenitors in Serum–Free Culture," Blood 81(6):1435–1441 1993.

Tsuji et al., "Enhancement of Murine Blast Cell Colony Formation in Culture by Recombinant Rat Stem Cell Factor, Ligand for c–kit," Blood 78(5):1223–1229, 1991.

Muramatsu, "The Midkine Family of Growth/Differentiation Factors," Develop. Growth & Differ. 36(1):1–8, 1994.

Naito et al., "Similarity of the Genomic Structure between the Two Members in A New Family of Heparin–Binding Factors," Biochemical and Biophysical Research Communications 183(2):701–707, Mar. 16, 1992.

* cited by examiner

Primary Examiner—Elizabeth Kemmerer
Assistant Examiner—Bridget E. Bunner
(74) Attorney, Agent, or Firm—Fish & Richardson P.C.

(57) ABSTRACT

The present invention provides novel use of the MK family that is used alone as an agent for proliferating hematopoietic stem cells and hematopoietic precursor cells. The invention also provides an agent for remarkably enhancing the above–described effect for promoting the proliferation of hematopoietic stem cells and hematopoietic precursor cells, comprising the MK family in combination with known hematopoietic factors such as IL–3, IL–6, G-CSF, GM-CSF, M-CSF, SCF, and EPO.

8 Claims, 17 Drawing Sheets

EXPANSION OF HEMATOPOIETIC CELLS USING MIDKINE OR PLEIOTROPHIN

CROSS REFERENCE TO RELATED APPLICATIONS

This application is a divisional application of U.S. application Ser. No. 09/214,569, now U.S. Pat. No. 6,383,480, which is a National Phase Application, filed Jan. 7, 1999, under 35 U.S.C §371, of International Application No. PCT/JP97/02401, filed Jul. 10, 1997.

TECHNICAL FIELD

This invention relates to a novel use of MK to promote proliferation and differentiation of hematopoietic stem cells and hematopoietic precursor cells in hematopoietic tissues, peripheral blood, or umbilical cord blood synergistically with other hematopoietic factors.

BACKGROUND ART

In blood, there exist various hemocytes having different shapes and functions, including erythrocytes, leukocytes, and platelets, which play important roles in maintaining homeostatis of the living body. These mature hemocytes have their own life-spans. For maintaining the hemocyte count at a constant level, hemocytes must be incessantly produced to make up for the number of hemocytes that is lost due to the expiration of their life-spans.

In the normal healthy individual, it is presumed that daily production of hemocytes reaches as much as $2 \times 10^{11}$ erythrocytes, $10^{11}$ leukocytes, and 1 to $2 \times 10^{11}$ platelets. Hematopoietic stem cells play central rolls in the system to produce such an enormous number of hemocytes over a long period without being exhausted. The cells have not only self-renewal capability but also multipotentiality to differentiate to various mature hemocytes including erythrocytes, granulocytes, platelets, and lympocytes. Hematopoietic stem cells (multipotential stem cells) lose their self-renewal capability as they proliferate to become hematopoietic precursor cells (committed stem cells) destined to differentiate to the specific hemocytes. Hematopoietic precursor cells then differentiate to mature peripheral hemocytes.

It has been known that a number of cytokines regulate each step of the hematopoietic system to proliferate and differentiate hematopoietic stem cells to various mature hemocytes via hematopoietic precursor cells. At least twenty kinds of the cytokines participating in the hematopoietic system have been found at present (Masami Bessho: Igaku no Ayumi 180(13): 802–806, 1997). The genes for all have been cloned, allowing their production on a large scale by genetic engineering techniques. Stem cell factor (SCF) and flk-2 ligand are the most remarkable cytokines as factors acting on mainly hematopoletic stem cells at the early stage of hematopoiesis. SCF acts on the most undifferentiated hematopoietic stem cells. In either mice or humans, it remarkably promotes the formation of colonies of blast colony-forming unit (CFU-BL), colony-forming unit-mixed (CFU-Mix), burst forming unit-erythrocyte (BFU-e), colony-forming unit-granulocyte/macrophage (CPU-GM), eosinophil colony-forming unit (CFU-Eo), and colony-forming unit-megakaryocyte (CPU-Meg); showing a synergistic effect with various cytokines such as IL-1, IL-3, II-4, IL-5, IL-6, IL-7, IL-11, G-CSF, GM-CSF, and EPO. It has been reported that SCF alone has weak colony-stimulating activity (Tsuji, K. et al., Blood 78: 1223,1991; Shioharu, M. et al., Blood 81: 1453, 1993; Kubo, T. and Nakahata, T., Int. Hematol. 58: 153, 1993). Nevertheless, SCF is thought to be the most important cytokine for in vitro amplification of hematopoietic stem cells at present.

The gene for flk-2 ligand has been just recently cloned and its biological activity has not been fully clarified. Since it exhibits synergistic actions with many cytokines as SCF does, it is expected to be an important factor for in vitro amplification of human hematopoietic stem cells.

Some of these hematopoietic factors have been clinically applied. For example, erythropoietin (EPO), which promotes the production of erythrocytes, is used for treating renal anemia, and granulocyte colony-stimulating factor (G-CSF), which promotes the production of neutrophils is used for treating neutropenia caused by cancer chemotherapy. These contribute to improved quality of life of patients. Recently, the clinical application of thrombopoietin (TPO) for treating thrombocytopenia has been studied because it promotes the production of platelets.

On the one hand, since hematopoietic stem cells are capable of reconstituting all kinds of cells in the hematopoietic system, the transplantation of hematopoietic stem cells has been widely performed for hematopoietic tumors. Recently, the transplantation of peripheral blood stem cells has rapidly become prevalent, and gathered attention as the powerful fundamental therapy for the chemotherapy-sensitive malignant tumors including the hematopoietic organ tumors. Furthermore, as a future prospect, the transplantation of hematopoietic stem cells is expected to be introduced to many cell therapy and gene therapy protocols. For that purpose, it is necessary to establish a method for amplifying hematopoietic stem cells in vitro. However, even now, human hematopoietic stem cells have been neither isolated nor clarified as to what extent they can repeat self-renewal.

DISCLOSURE OF THE INVENTION

An objective of the present invention is to provide a novel cytokine capable of synergistically promoting the proliferation and differentiation of hematopoietic stem cells or hematopoietic precursor cells in combination with known cytokines.

Another objective of the present invention is to provide a novel cytokine capable of promoting the proliferation and differentiation of granulocyte/monocyte precursor cells.

Still another objective of the present invention is to provide a novel cytokine capable of promoting the proliferation and differentiation of erythroblast precursor cells in combination with known cytokines.

The present inventors have found that single use of a novel growth factor called midkine (MK) or pleiotrophin (PTN) promotes the proliferation and differentiation of hematopoietic stem cells and hematopoietic precursor cells (also called hematopoietic cells) of mammals such as mice and humans in vitro. MK also exerts an extremely remarkable synergistic effect for proliferating and differentiating hematopoietic cells when used together with SCF, M-CSF, G-CSF, GM-CSF, IL-3, and IL-6. Furthermore, the inventors have found that MK or PTN promotes rapid recovery of neutrophils in neutropenia of mammals.

The present invention will be described in detail below.

MK was isolated as the product of a gene that is expressed at the early stage of the differentiation of mouse embryonic tumor cells by the induction of retinoic acid (Kadomatsu, K., et al., Biochem. Biophy. Res. Commun. 115: 1312–1318, 1988). PTN was found as a heparin-binding protein with neurite outgrowth capability in the newborn rat brain (Rauvaa, H., EMBO J. 8: 2933–2941, 1989). MK and PTN belong to a new class of heparin-binding growth factors, sharing a 45% homology (in amino acid sequence) to each other, and called the MK family. MK and PTN respectively exhibit characteristic expression patterns in the developmental process, indicating that they have important physiological activities for the implementation of differentiation.

Paying attention to such biological activities of the MK family, the present inventors studied their hematopoietic factor activities to proliferate and differentiate myeloid cells and peripheral blood stem cells of mammals. In general, at what stage of the proliferation/differentiation process of hematopoietic stem cells and hematopoietic precursor cells in myeloid hematopoietic factors participate and function can be studied by culturing a certain number of myelocytes in a semi-solid medium in the presence of these hematopoietic factors, selecting cells constituting colonies formed, and counting the number of colonies. In such colony formation methods, it has been proved by a number or direct or indirect methods that, a single hematopoietic precursor cell profliferates, divides, and matures, forming a single colony comprising many matured hemocytes. There are colony formation assay methods specific for cells of each hematopoietic system including granulocyte/macrophage, erythroblasts, and megakaryocytes, and stimulators specific for each hematopoietic system are used.

Precursor cells of the granulocyte/macrophage system, CFU-GM, differentiate to precursor cells of neutrophil system, CFU-G, and precursor cells of monocytes, CFU-M. For that purpose, colony-simulating factors (CSF) specific to each precursor cell must be present. More specifically, GM-CSF is required for CFU-GM, G-CSF for CFU-G, and M-CSF for CFU-M. Some of these CSFs not only differentiate precursor cells to mature cells but also activate the function of matured hemocytes.

CFU-GM can be cultivated by either the soft agar method or the methylcellulose method using bone marrow nucleated cells. Since colonies formed by either method are constituted by a cell population of granulocytes and macrophages at various developmental stages, precursor cells one step further differentiated from hematopoietic stem cells are to be examined. Picking up and staining of these colonies revealed the presence of G colony consisting of granulocytes, M colony consisting of macrophages, and GM colony consisting of the mixture of both. In humans, colonies are rather small and classified into a group called a colony containing 40 cells or more and a group called a cluster with a lower accumulation of cells than a colony.

In order to examine whether MK has the activity causing myelocytes to proliferate, the proliferation of mouse myelocytes was assayed by the MTT method, resulting in enhancing the proliferation 1.6- to 2-fold in the system supplemented with MK at the concentrations of 5, 50, 500, and 5000 ng/ml as compared with the system without MK. A concentration-dependent elevation of the activity was observed in the range of 5 to 500 ng/ml MK.

In the colony assay for human peripheral blood mononuclear cells in the presence of various cytokines, as shown in FIG. 1, colonies were not formed at all in the system without cytokines, but formed in the system supplemented with MK similarly as with GM-CSF and IL-3. The colony size tends to be larger in the system with MK added than in the systems with cytokines such as G-CSF, GM-CSF, and IL-3 added. These results indicate that MK alone has the activity to maintain the viability of human peripheral blood stem cells or hematopoietic precursor cells, or promote their proliferation. Furthermore, the combined use of MK with other cytokines such as M-CSF, G-CSF, GM-CSF, IL-3, and IL-6 synergistically promotes colony-forming capability. For example, the number of colonies increase 7 to 9-fold in the cases of combined use of MK with G-CSF, GM-CSF, or IL-3 as compared with those of the single use of MK, G-CSF, GM-CSF, or IL-3. Also, the combination of MK+G-CSF+IL-3+IL-6 remarkably increased the number of colonies formed as compared with that of GM-CSF+IL-3+IL-6, and the combination of MK+G-CSF+IL-6 significantly increased the number of colonies as compared with that of G-CSF+IL-6. In another experiment using a source of human peripheral blood mononuclear cells different from that used for the experiments described in FIG. 1, treatment with MK, GM-CSF, or IL-3 alone produced primarily GM colonies, while use of G-CSF alone produced primarily G colonies. Combinations of MK+G-CSF+GM-CSF, or of MK+G-CSF significantly increased the number of G colonies as compared with the use of G-CSF alone. That is, MK is considered to synergistically promote the proliferation, differentiation and maturation of CFU-GM of G-CSF, increasing the number of neutrophils in the peripheral blood.

When cells after 2-week liquid culture of human peripheral blood stem cells in the presence of various cytokines were examined by specific staining, there were observed, as shown in FIG. 3, predominantly many granulocytes (neutrophils) in the system supplemented with MK, clearly indicating the action of MK on the proliferation of neutrophils. Especially, in the case of the combination of MK+G-CSF+GM-CSF+SCF+IL-330 IL-6, there were observed an extremely remarkable promotion of the proliferation and differentiation of neutrophils.

Also, in the colony assay performed after the above-described liquid culture, the cell adherence to a culture dish increased in the system supplemented with MK as compared with that without MK, indicating that MK also promotes the proliferation of the interstitial cell system (stroma cell system). In the case of IL-6 alone, colonies formed were of macrophages, and in the case of MK+IL-6, half of colonies formed were of granulocytes. These results indicate the participation of MK in the promotion of proliferation and differentiation of granulocytes.

Whether such a remarkable promotion by MK of the production of neutrophils is displayed in vivo can be studied by administering MK to a mouse whose hematopoietic system has been damaged by administration of an anticancer drug, or exposure to radiation, and examining the recovery state of neutrophilis. MK was administered to a mouse daily for 13 consecutive days, and on the $5^{th}$ day after the initiation of administration, an anticancer drug, Cyclophosphamide (CY), was administered to the mouse. Examination of hemocytes in the blood collected from the mouse at appropriate intervals revealed a remarkable promotion of the recovery of the number of neutrophils as expected (Table 1).

TABLE 1

| | Leukocyte count (μ/l) | | | | | | Neutrophil count (μ/l) | | | | |
|---|---|---|---|---|---|---|---|---|---|---|---|
| Day | 0 | 2 | 4 | 7 | 9 | Day | 0 | 2 | 4 | 7 | 9 |
| Control | 6100 | 6400 | 6820 | 8220 | 5120 | Control | 1580 | 1663 | 2046 | 2606 | 1204 |
| CY | | 2000 | 1040 | 4020 | 6560 | CY | | 1330 | 111 | 2471 | 4203 |
| CY + MK | | 1840 | 1100 | 10460 | 7640 | CY + MK | | 1077 | 91 | 7013 | 5486 |
| MK | 6780 | 7500 | 4520 | 6460 | 5100 | MK | 1438 | 2920 | 1652 | 2201 | 2277 |

| | Lymphocyte count (μ/l) | | | | | | Erythrocyte (×10$^4$/mm$^3$) | | | | |
|---|---|---|---|---|---|---|---|---|---|---|---|
| Day | 0 | 2 | 4 | 7 | 9 | Day | 0 | 2 | 4 | 7 | 9 |
| Control | 4383 | 4391 | 4581 | 5370 | 3771 | Control | 701 | 667 | 810 | 832 | 858 |
| CY | | 510 | 866 | 1220 | 2034 | CY | | 670 | 708 | 687 | 713 |
| CY + MK | | 680 | 988 | 2335 | 1596 | CY + MK | | 751 | 679 | 598 | 670 |
| MK | 4700 | 3996 | 2720 | 3846 | 2597 | MK | 818 | 783 | 792 | 813 | 818 |

The action of MK on hematopoietic cells under the conditions closer to in vivo can be examined by, for example, the colony assay using a methylcellulose medium containing EPO, IL-3, IL-6, and SCF [MethoCult GF M3434 (Stem Cell Technologies, Inc.)]. This medium (hereinafter called M3434 medium) can proliferate and differentiate precursor cells of erythrocytes, leukocytes, and platelets.

Results of the colony assay for mouse spleen cells in the system of the M3434 medium supplemented with MK are shown in FIGS. 4 and 5. FIG. 4 illustrates the number of CFU-GM colonies or CFU-G colonies. Although CFU-GM colonies or CFU-G colonies can be formed with the M3434 medium alone, the number of colonies generally increases in the system supplemented with the MK as compared with the M3434 medium alone. Especially, when MK is added at the concentration of 1 to 10 ng/ml, the colony number remarkably increased 2 to 3-fold on the 8$^{th}$ and 10$^{th}$ day of the assay. FIG. 5 illustrates the number of colony-forming unit-mixed (CFU-Mix). CFU-Mix are multipotential stem cells at a slightly differentiated stage, having lower self-renewal capability than blast colony-forming units (CFU-BL) which are the most undifferentiated cells identifiable by the in vitro colony assay and are thought to contain cells capable of differentiating to erythrocytes, leukocytes, and platelets. In the system supplemented with MK, CFU-Mix colony significantly increased in number. That is, MK, at least by its combined use with IL-3, IL-6, SCF and EPO, is thought to significantly promote the proliferation and differentiation of hematopoietic stem cells or immature hematopoletic cells close to them. These activities are thought to be very useful for the proliferation of hematopoietic stem cells in vitro for the transplantation of bone marrow and peripheral blood stem cells, or gene transfer to hematopoietic stem cells.

In the hematopoietic cells, the more mature peripheral blood cells are, the more sensitive to anticancer drugs. Utilizing this property, the present inventors attempted to concentrate hematopoietic stem cells or hematopoietic precursor cells by an anticancer drug. Namely, the colony assay was performed using spleen cells of a mouse, to which Cyclophosphamide had been administered. Results are shown in FIGS. 6 and 7. FIG. 6 shows the number of CFR-Mix and CFU-G colonies increased 2-fold or more in the system supplemented with MK as compared with the system without MK. This experiment also indicates that MK promotes the proliferation of hematopoietic stem cells and hematopoietic precursor cells.

The effect of MK was investigated using peripheral hemocytes from a patient with non-Hodgkin's lymphoma and a MethoCult H4230 medium (consisting of methylcellulose (0.9), 2-mercaptoethanol (10 to 4 M), L-glutamine (2 mM), fetal bovine serum (30%), and bovine serum albumin (1%), and containing neither CSF nor EPO; Stem Cell Technologies Inc.). The colony assay was performed using the following combinations; MethoCult H4230 alone, H4230+MK, H4230+G-CSF, and H4230+MK+G-CSF. The proportion of CD34 positive cells in peripheral stem cells from the patient was 1.4%. Results are shown in FIG. 8. Although no colonies were formed with MK alone, a remarkable colony-forming capability was manifested in the case of MK+G-CSF, and the number of colonies was clearly twice or more as hight as that in the case of G-CSF alone. On and after the 10$^{th}$ day of the initiation of assay, the increase in number of colonies tends to reduce in the MK+G-CSF group as compared with the group of G-CSF alone. Microscopic observation of colonies on and after the 10th day revealed a tendency that the conoly maturation was accelerated in the MK+G-CSF group as compared with the G-CSF alone group. Therefore, the deceleration of the increase in number of colonies in the MK+G-CSF group as compared with the G-CSF alone group is probably attributed to the accelerated maturation of colonies.

It is noteworthy that, in the above-described colony assay, the size of each of colonies formed was always larger in groups supplemented with MK as compared with groups with no MK added. In order to study this fact quantitatively, three each of large colonies formed on the 14th day in the presence of MK alone, G-CSF alone, and MK+G-CSF in the colony assay of peripheral blood stem cells from the above-described patient were selected, sucked up under a microscope, and counted for their constituting cells with a hemocytometer to calculate mean values. Results are shown in FIG. 9. It is obvious that colonies formed with MK+G-CSF contain more cells than those formed with G-CSF alone. That the size of colony is large means that the number of constituting cells is also large. From these results, it is evident that MK acts on the proliferation and differentiation of hematopoietic stem cells and hematopoietic precursor cells.

The colony assay was similarly performed with the peripheral blood from a healthy normal individual. The proportion of CD34-positive cells in the peripheral blood of this subject was 0.4%. Results are shown in FIG. 10. Colonies were formed with MK alone, On the 10$^{th}$ and 14$^{th}$ days, the number of colonies increased MK concentrationdependently. The MK+G-CSF system produced at the highest 2 or more times as many colonies as the system of G-CSF alone. These results clearly shows that, when MK was added, the same tendency was obtained regardless of whether cells are derived from a healthy normal individual or a patient.

Furthermore, the colony assay was similarly performed using the peripheral blood from the above-described healthy normal individual in the presence of pleiotrophin (PTN), which is another member of the MK family. PTN used herein was a recombinant PTN (pleiotrophin, recombinant human (Sf21-derived); (Lot GH055011) (R & D Systems)). Results are shown in FIG. 11. PTN alone exhibited the colony-forming capability of MK and the number of colonies formed was markedly high. A synergistic action of PTN with G-CSF to promote the colony formation was similarly observed as in the case of MK. From these results, PTN obviously promotes the proliferation and differentiation of hematopoietic stem cells and hematopoietic precursor cells like MK.

Next, using a hematopoietic stem cell assay medium complete type (Lot No. 96101601; Kyokuto Seiyaku Kogyo) containing IL-3, SCF, G-CSF, and EPO, the colony assay was carried out with peripheral blood cells from a healthy normal individual. This assay is considered to be performed under conditions closer to in vivo. Results with MK are shown in FIGS. 12 and 13, and those with PTN in FIGS. 14 and 15. No increase in BFU-E was observed with any combinations including MK+IL-3, MK+SCF, and MK+G-CSF. However, the combinations of MK+EPO and PTN+EPO were assumed to increase BFU-E. Erythroblast precursor cells, BFU-E, were formed on the 14th day of culture, and are known to be more undifferentiated than CFU-E formed on the 5th to 7th days. Addition of MK or PTN to a Kyokuto complete medium resulted in formation of at the highest 2 or more times as many BFU-E as the complete medium alone on the 12th day after the initiation of culture. These results indicate that at least the addition of MK to the complete medium results in promoting the proliferation of erythroblasts as well. As described above, it is evident that the MK family is capable of acting on hematopoietic stem cells and hematopoietic precursor cells in the hematopoietic tissues of mammals to maintain, proliferate, and differentiate them, and synergistically or additionally enhancing the above-described functions by the combined use with various cytokines such as SCF, M-CSF, G-CSF, GM-CSF, IL-3 AND IL-6. Especially, the MK family remarkably promotes the proliferation of CFU-Mix which is very close to multipotential stem cells, under conditions closer to in vivo. The MK family also promotes the proliferation and differentiation of granulocyte/macrophage precursor cells and exerts the remarkable neutrophil increasing effect in an in vivo neutropenia model. This MK family alone or in combination with more than one cytokine including SCF, M-CSF, G-CSF, GM-CSF, IL-3, and IL-6 can be clinically applied and, especially, used for the ex vivo expansion of hematopoietic stem cells in the transplantation of bone marrow and stem cells derived from the peripheral blood and umbilical cord blood. In addition, the MK family is expected to be used for the treatment of patients with and prevention of neutropenia, refractory anemia, and leukemia caused by cancer chemotherapy. Furthermore, the MK family would be used in the future for proliferating stem cells for gene therapy targeting hematopoietic stem cells; Especially, it is very promising to increase the dose density in cancer chemotherapy by the combined use of MK with G-CSF, improving effects of chemotherapy by increasing the dose of antitumor drugs or shortening the administration period.

MK and PTN used in the present invention can be either a natural or recombinant product. The recombinant MK family means a substance well homologous with the natural MK or PTN and having biological activities equivalent thereto. Such MK or PTN includes their derivatives and analogues. The purified MK or PTN of mammals means those derived from mice or humans, but not limited thereto. MK or PTN of this invention also includes glycosylated and non-glycosylated MK or PTN.

BEST MODE FOR IMPLEMENTING THE INVENTION

Figure 1:
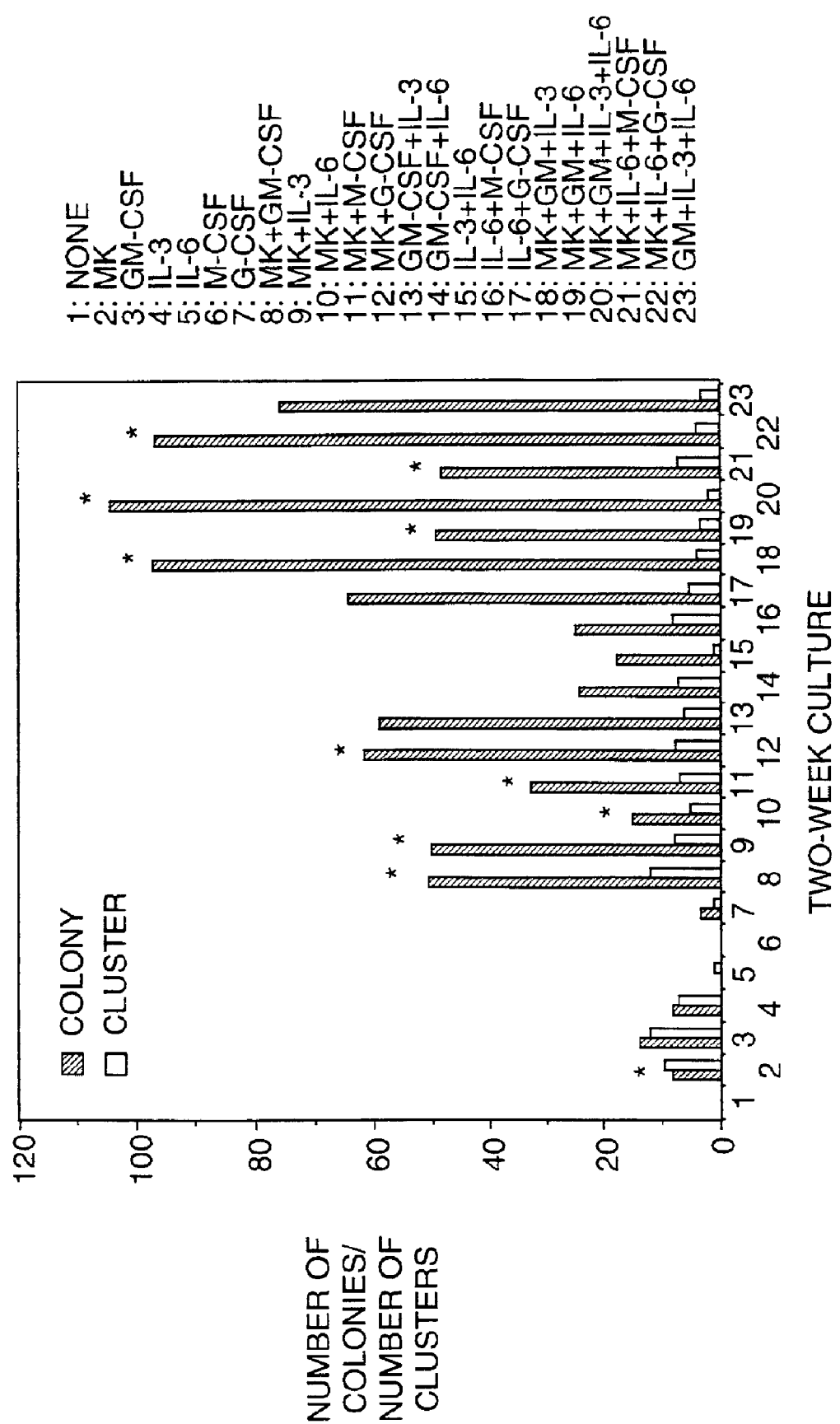
FIG. 1 illustrates the effects of single or combined use of MK, G-CSF, GM-CSF, M-CSF, IL-3, and IL-6 on the colony-forming capability of human peripheral blood mononuclear cells.

The present invention will be described below with reference to examples, but is not to be construed to be limited thereto. MK used here is human MK described in SEQ ID NO: 3 in Japanese Patent Application No. Hei 7-255354.

EXAMPLE 1

Effect of MK on Promoting Neutrophil Recovery in a Neutropenia Model.

Neutropenia is a disease wherein neutrophils that play the most important role in preventing infection are selectively lost or significantly reduced in member. In the following is presented an example, wherein MK was administered in a neutropenia model prepared by administering an antitumor drug to normal mice and examined for its effect on promoting neutrophil recovery.

Neutropenia model mice were prepared by administering an antitumor drug, Cyclophosphamide (CY) to 12-week-old ICR mice (male). The mice were divided into the following groups so that each group had five mice; (1) untreated group (control group), (2) CY-administered group, (3) CY+MK-administered group, and (4) MK alone administered group. MK was diluted with physiological saline and intraperitoneally administered to the mice daily at a dose of 0.1 ml/animal and 300 $\mu$g/kg for 13 consecutive days. Six house after the administration on the 5th day of the consecutive administration, CY was administered to the mice at a dose of 266 mg/kg, corresponding to $\frac{2}{3}$ of the $LD_{50}$ value. The day of CY administration was taken as Day 0, and the blood was collected five times in total, namely on Day 0, Day 2, Day 4, Day 7, and Day 9, and counted for leukocyetes, neutrophils, lymphocytes, and erythrocytes. Results are shown in Table 1. The number of lymphoytes reached the lowest value on Day 2 in the CY-administered group and the CY+MK-administered group as compared with the control group, and did not recover until Day 9. The number of neutrophils reached the lowest value on Day 4, but elevated to 2.8 times as high as that of the control group on Day 7.

EXAMPLE 2

Colony Formation Promoting Action of MK and Other Cytokines on Human Peripheral Blood Mononuclear Cells For collecting human peripheral blood stem cells (PBSC), it is necessary to let them migrate from the bone marrow to the peripheral blood. A hematopoietic factor, G-CSF, was administered to an individual, who was in a hematologically stable condition, to induce migration of PBSC to the peripheral blood, and the blood was collected with a heparinized syringe. The peripheral blood was fractionated using a separation agent. The mononuclear cell layer thus fractionated was mixed with phosphate buffer (PBS), and centrifuged at 4° C. and 1500 rpm for 5 min. After the centrifugation, the supernatant was discarded and cells were washed by repeating this procedure several times. The cells were suspended in a medium containing 10% FBS and counted with a hemocytometer K-8000. Finally, the cell concentration was adjusted to $1\times10^6$/ml with a medium containing 10% FBS.

Test substances used were MK, 50 $\mu$g/ml; G-CSF, 10 ng/ml; GM-CSF, 10 ng/ml; M-CSF, 50 ng/ml; IL-3, 10 ng/ml; IL-6, 100 ng/ml; and SCF, 10 ng/ml. These substances were adjusted to the above concentrations by preparing each solution at 10-fold concentration of the final concentration using Iscove's Modified Dulbecco's Medium (IMDM) and adding it to an assay system in an amount of 10% of the total volume of the system.

A methylcellulose medium containing FBS was used for the colony assay. A methylcellulose solution was prepared by adding to the medium methylcellulose powder (3500 to 5600 cps, Tokyo Kasei Kogyo) to 2%.

A necessary amount of each solution prepared as described above was placed in a single tube. Namely, in each tube, solutions were mixed to give final concentrations of $1\times10^5$/ml for cells, 20% for FBS, 20% for the medium containing 10% FBS, and 0.8% for methylcellulose. The test substances were then respectively added to this mixture to give the above-described concentrations. After the resulting mixture was thoroughly vortexed, it was inoculated onto a plastic culture dish (Falcon, 1008) using a syringe with a #18 needle and cultured in a 5% carbon dioxide incubator at 100% humidity and 37° C. for 2 weeks. After two weeks, the number of colonies formed was counted using an inverted microscope. Results are shown in FIG. 1.

Figure 2A:
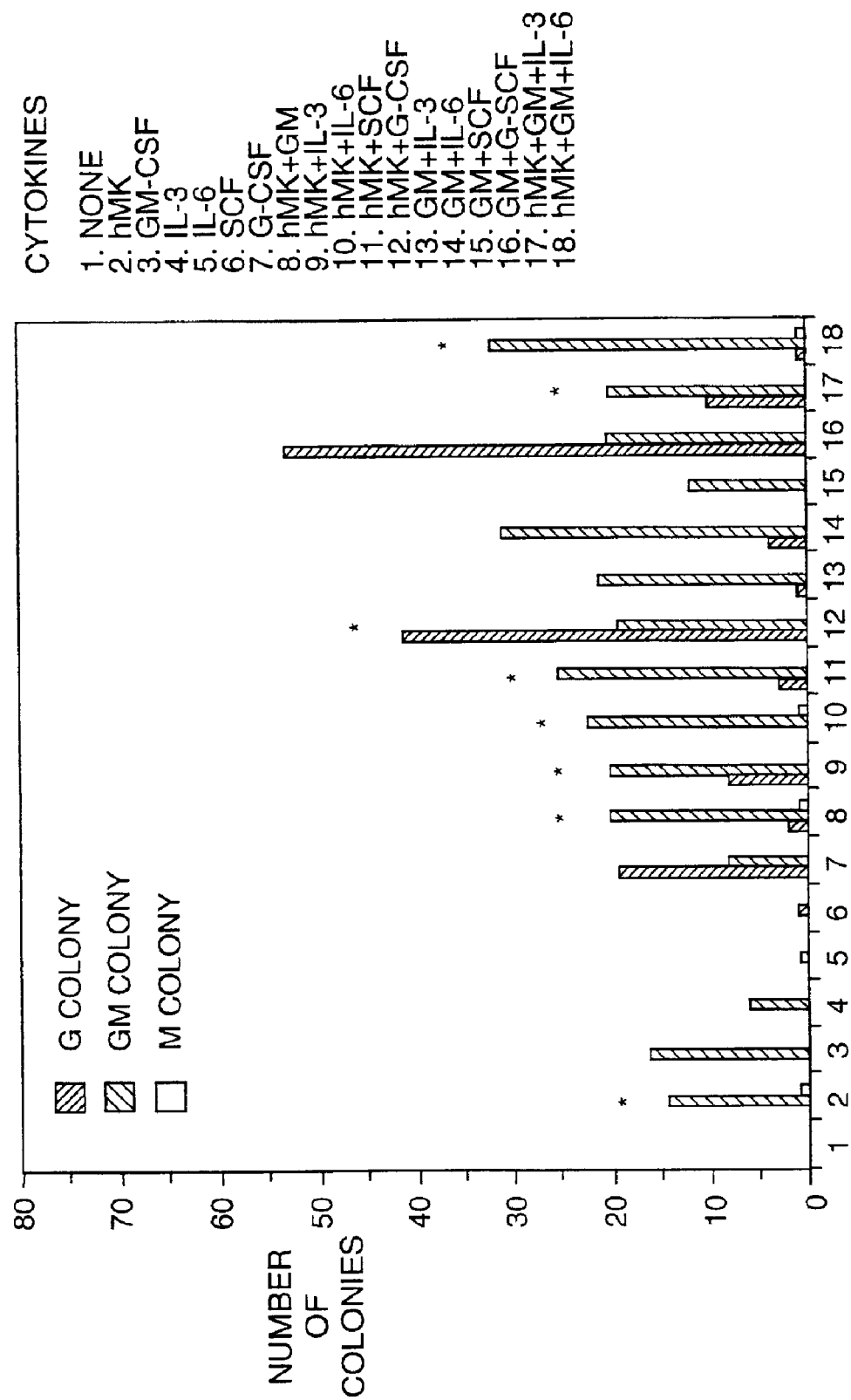
FIGS. 2A and 2B illustrate effects of single or combined use of MK, G-CSF, GM-CSF, M-CSF, IL-3, IL-6 and SCF on G colony, GM colony and M colony-forming capabilities of mononuclear cells in human peripheral blood different from that used in the experiment in FIG. 1.
Figure 2B:
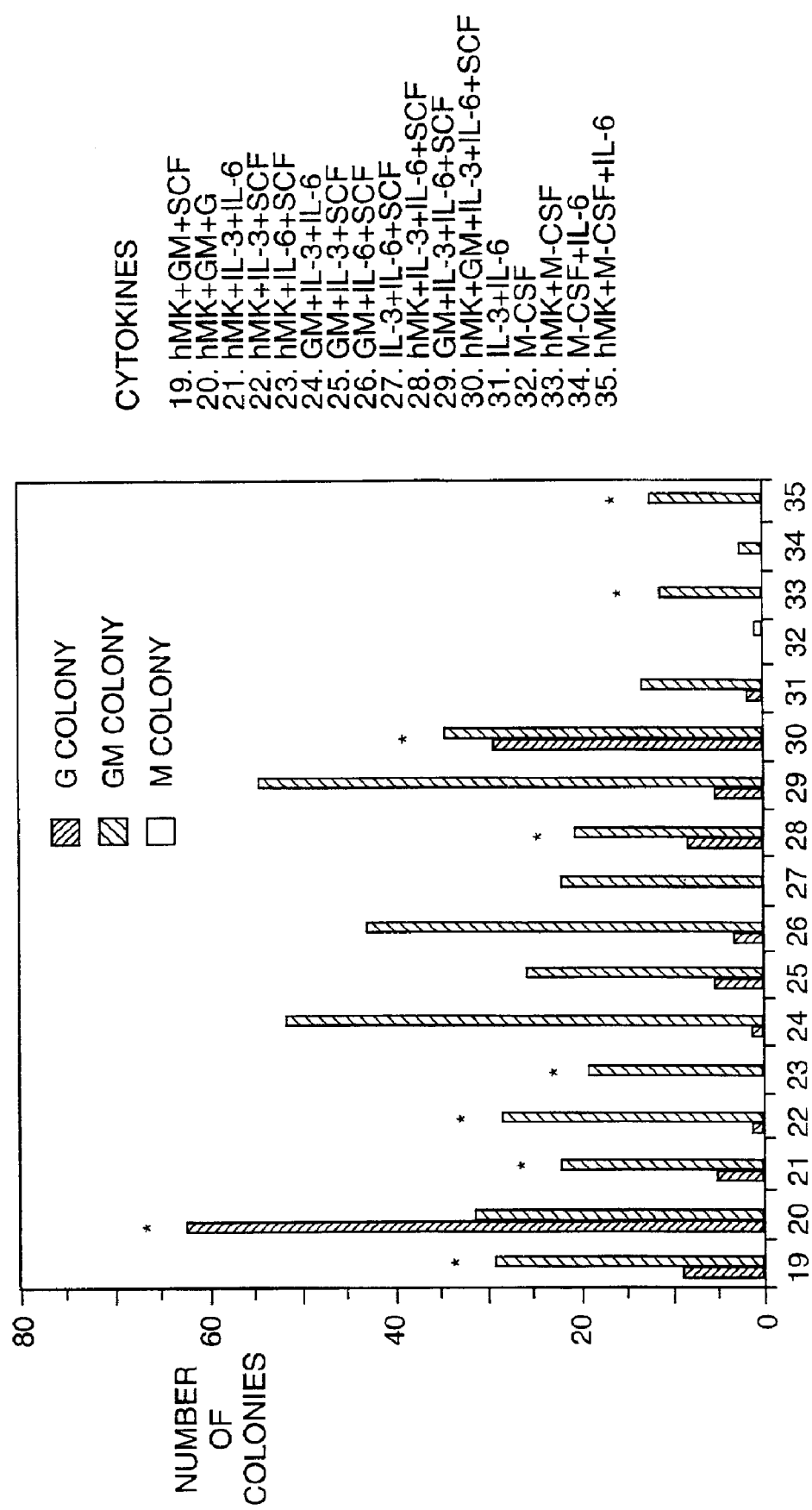

The colony assay of peripheral blood mononuclear cells from another healthy normal individual using G-CSF, GM-CSF, and M-CSF was performed by a similar method as described above. Results are shown in FIG. 2.

EXAMPLE 3

Liquid Culture of Human Peripheral Blood Mononuclear Cells in the Presence of MK and Other Cytokines Human peripheral blood mononuclear cells and test substances were prepared as in Example 2. The test substances were respectively added to the mixture containing $1.5\times10^5$/ml of cells, 30% of FBS, and 10% of the medium containing 10% BSA to give the above-described concentrations. The resulting mixture was distributed onto a plastic culture dish (Falcon, 1008) and cultured in a 5% carbon dioxide incubator at 100% humidity and 37° C. for 2 weeks.

After 2 weeks, all cells were recovered from each culture dish. Cells adhering to the culture dish were recovered by treating them with 0.25 trypsin/EDTA. Cells were recovered in tubes and centrifuged once at 4° C. and 800 rpm. The cells were suspended in the same volume of the culture medium and counted with a hemocytometer.

Figure 3A:
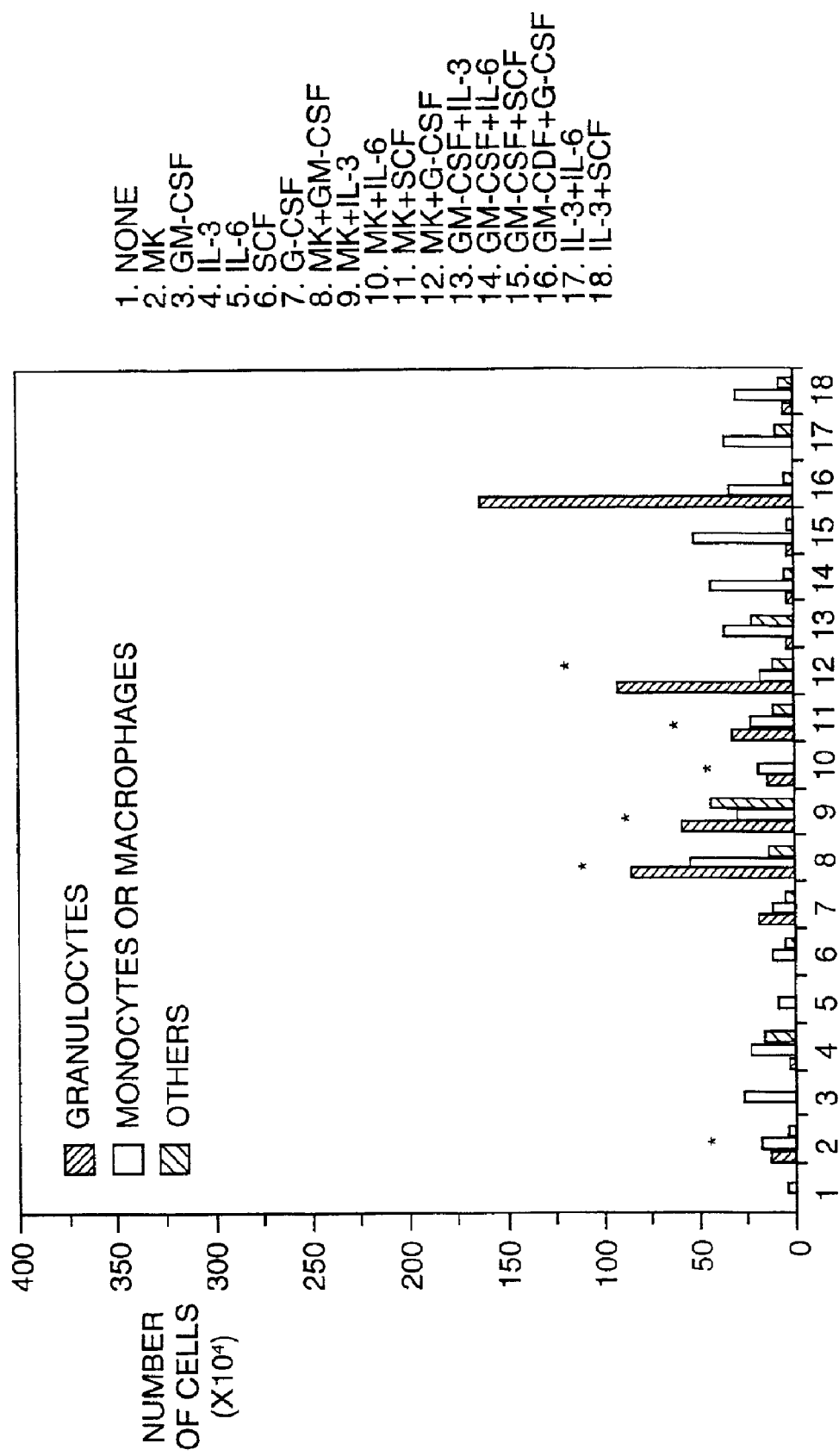
FIGS. 3A and 3B illustrate numbers of granulocytes, monocytes, or macrophages, and other cells counted by the esterase double staining of human peripheral blood mononuclear cells after two-week liquid-culture in the presence of MK, G-CSF, GM-CSF, IL-3, IL-6, and SCF alone or in combination.
Figure 3B:
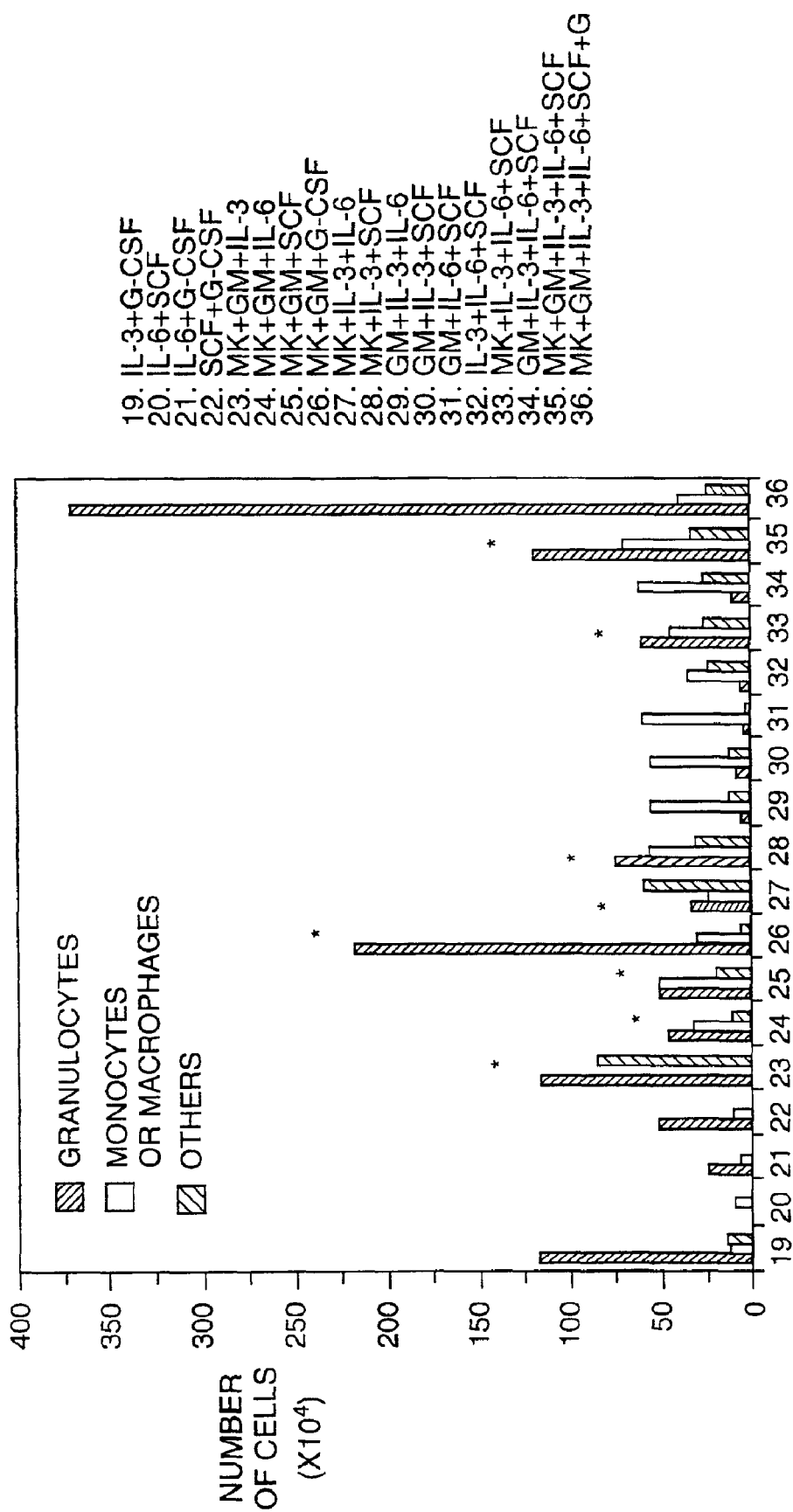

The cells collected for counting were mounted onto a slide glass with a Cytospin (Cytospin 2; SHANDON) and subjected to the esterase double staining (an esterase staining kit and esterase AS-D staining kit, Muto Kagaku Yakuin). Changing the field of vision, cells were distinguished as granulocytes, monocytes, macrophages, and others according to the staining. Results are shown in FIG. 3.

EXAMPLE 4

Hematopoiesis Promoting Action of MK Under Conditions Closer to in Vivo

The spleen of 8-week-old BDF1 mouse (female) was aseptically excised on a clean bench, and cells were pressed out using a needle (Therumo, 22G×1¼" (0.70×32 mm)) into IMDM (GIBCO BRL) in a petri dish. Cells in the spleen were collected into IMDM (10 ml) in a tube, thoroughly mixed by pipetting, and passed through a cell strainer (FALCON 2350, 70 μm) Mononuclear cells were counted with a hemocytometer, adjusted to a concentration of $1 \times 10^6$ cells/ml with IMDM to serve as a cell suspension. Test solutions containing MK at 100 ng/ml, 1 mg/ml, and 10 mg/ml in IMDM were similarly prepared.

Figure 4:
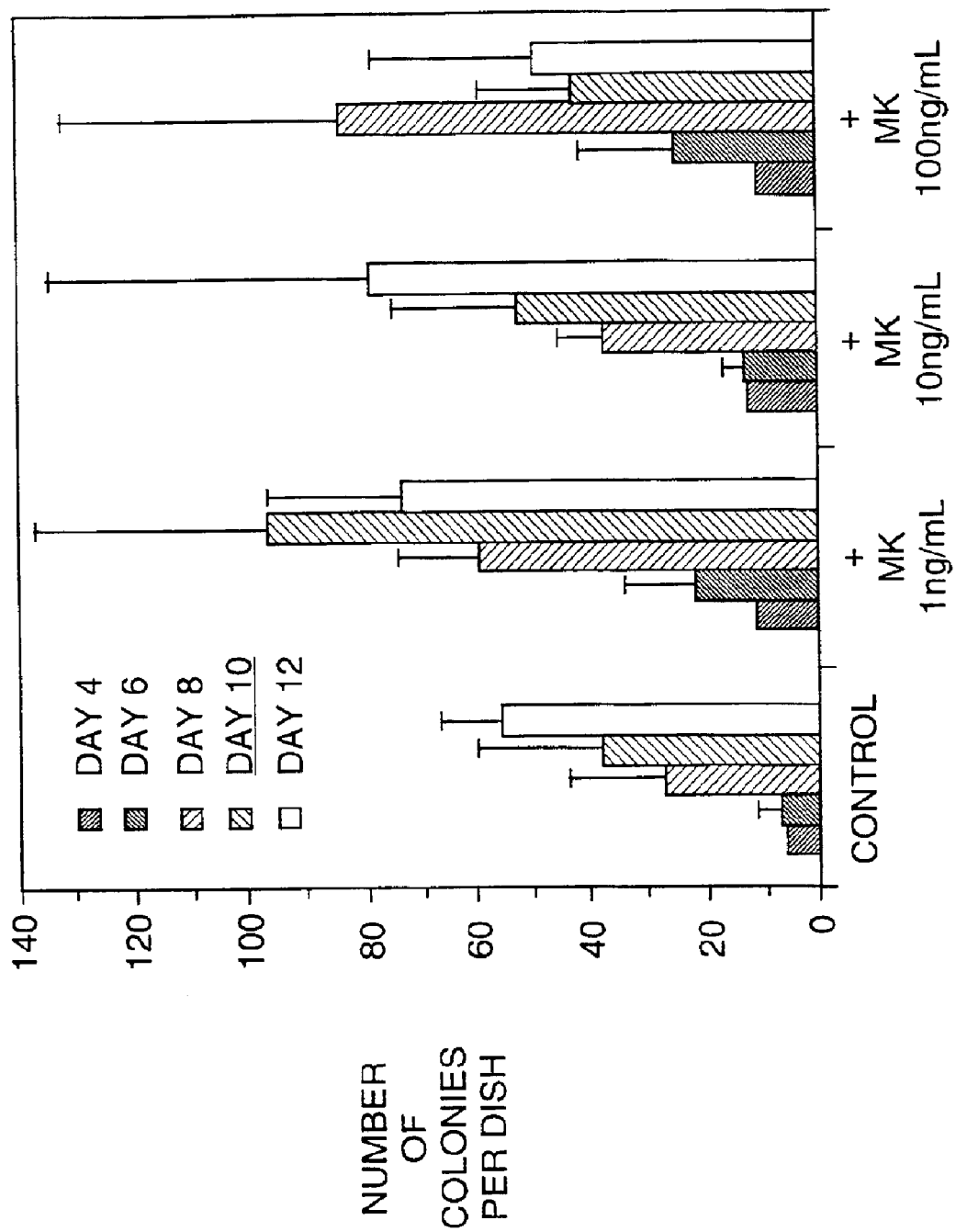
FIG. 4 illustrates effects of MK on colony-forming capability of mouse spleen cells cultured in a complete methylcellulose medium containing EPO, IL-3, IL-6, and SCF (MethoCult GF M3434) supplemented with MK for 12 days in order to examine the proliferation promoting action of MK on hematopoietic cells under conditions closer to in vivo.
Figure 5:
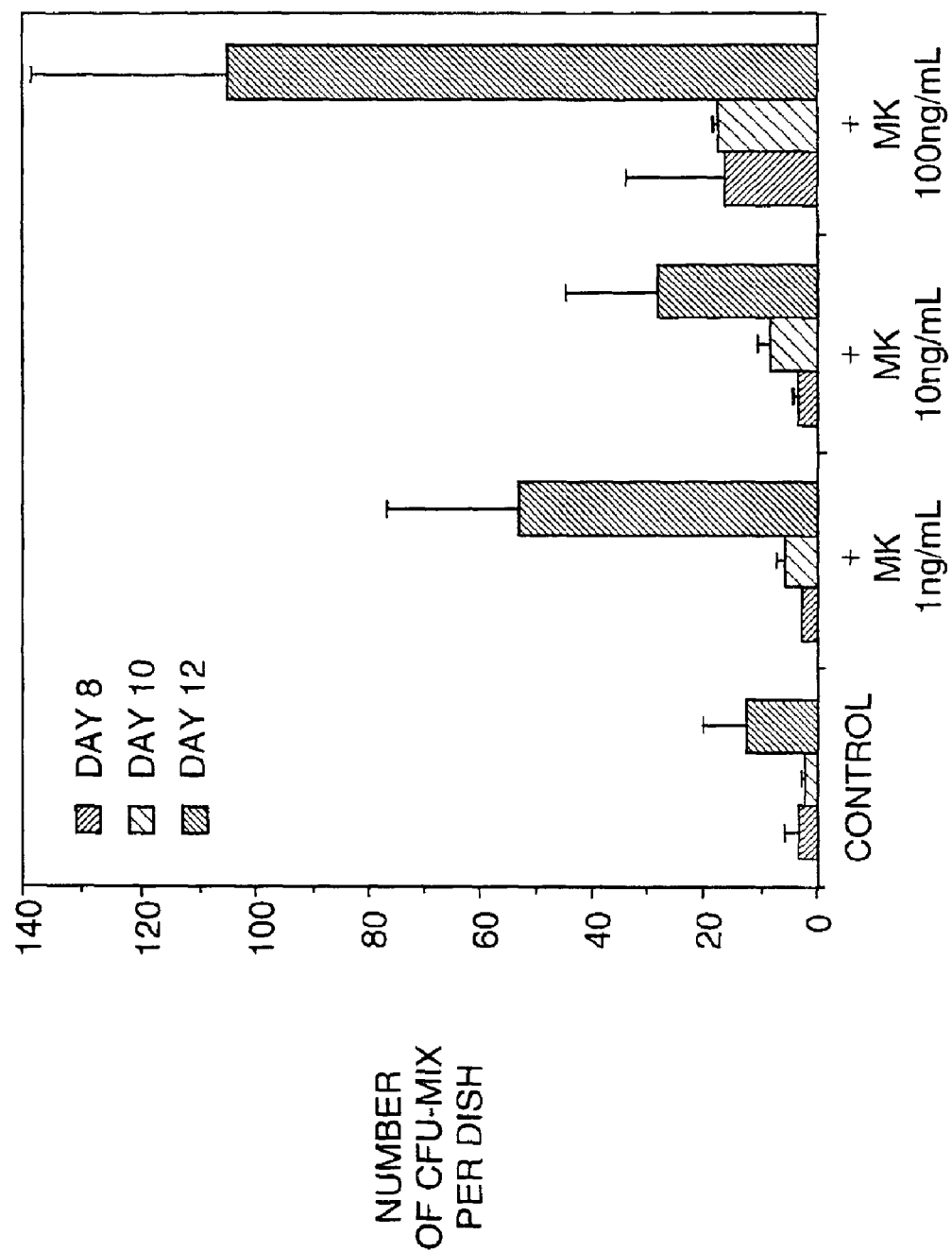
FIG. 5 illustrates effects of MK on CFU-Mix colony-forming capability in an experiment similar to that in FIG. 4.

The methylcellulase medium used was a complete medium, MethoCult GF M3434 (containing 0.9% methylcellulose, 10 to 4 M 2-mercaptoethanol 2 mM L-glutamine, FBS, 1% BSA, EPO, insulin, transferin, IL-3, IL-6 and SCF; Stem Cell Technologies, Inc.). To the medium were added the above-described cells to $1 \times 10^5$/ml and MK to a final concentration of 1, 10, or 100 ng/ml. The colony assay was then performed by a method similar to that in Example 2. Results are shown in FIGS. 4 and 5.

EXAMPLE 5

Hematopoiesis Promoting Action of MK under Conditions Closer to in Vivo (Concentration of Hematopoietic Stem Cells and Hematopoietic Precursor Cells)

Figure 6:
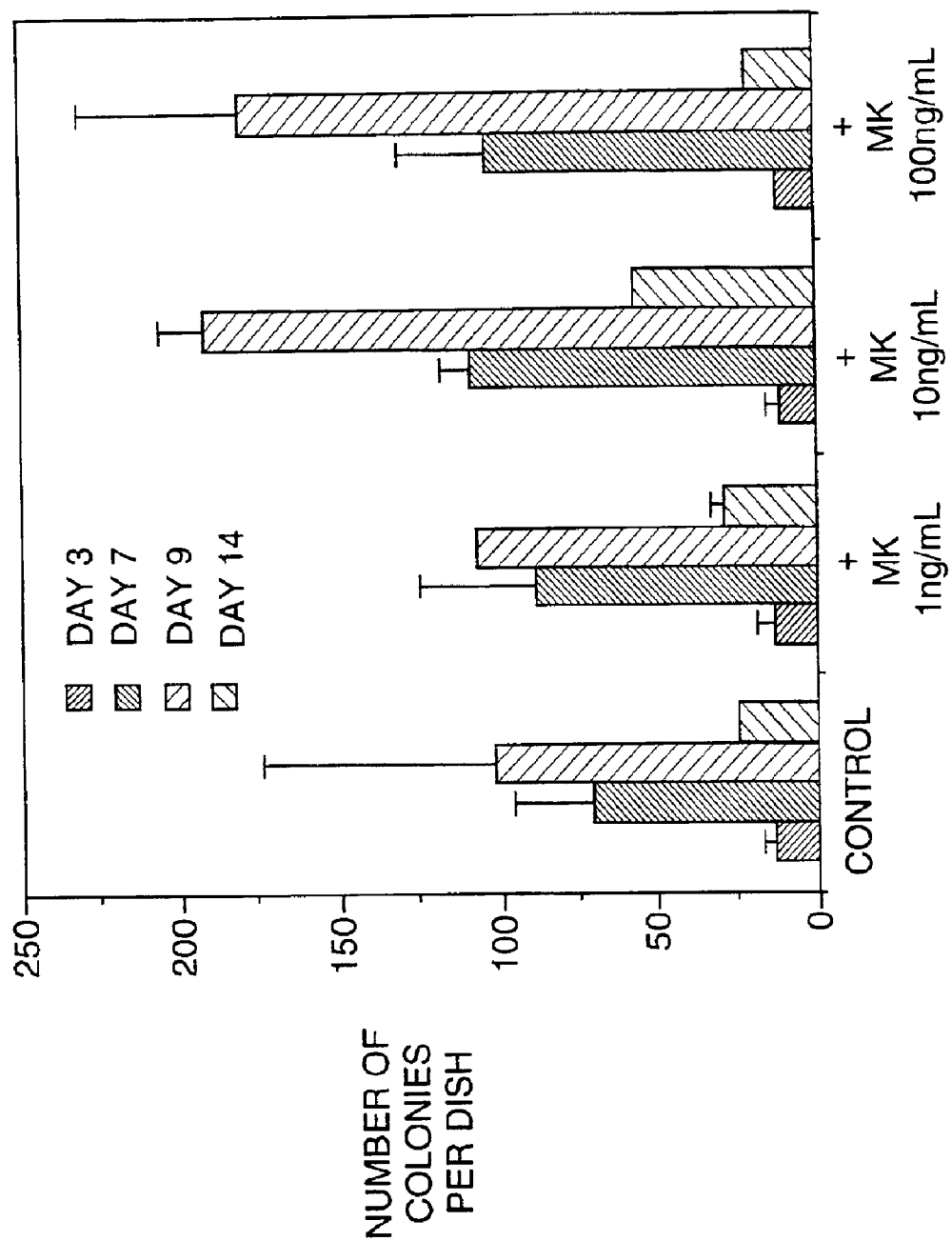
FIG. 6 illustrates effects of MK on CFU-G colony-forming capability when an anticancer drug, Cyclophosphamide, was administered to a mouse, and myelocytes were isolated on the 4th day after the drug administration and cultured in a complete methylcellulose medium containing EPO, IL-3, IL-6, and SCF (MethoCult GF M3434) supplemented with MK for 14 days.
Figure 7:
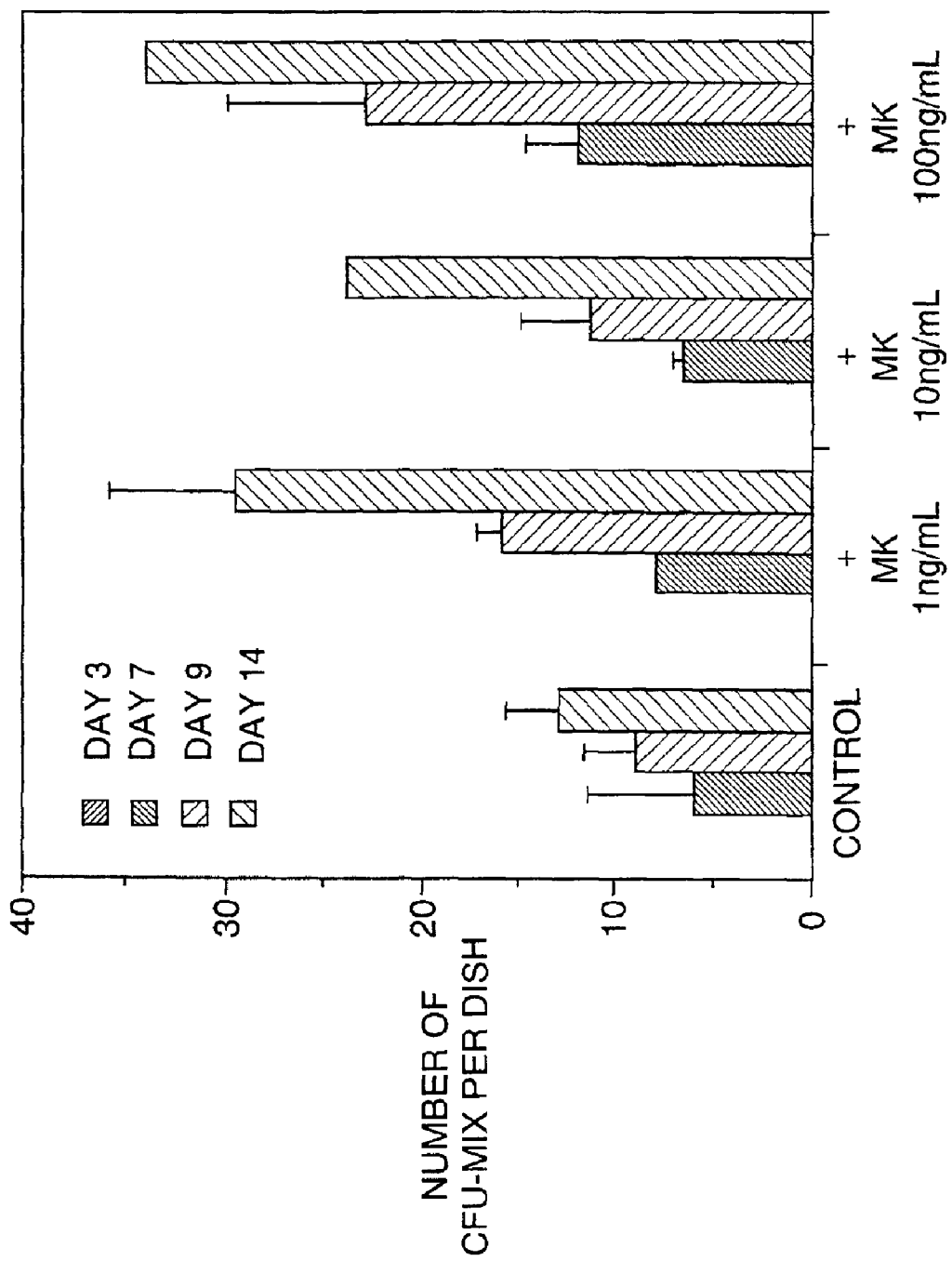
FIG. 7 illustrates effects of MK on CFU-Mix colony-forming capability in an experiment similar to that in FIG. 6.

To concentrate hematopoietic precursor cells in myelocytes, Endoxan powder (a powerful drug according to the Japanese Pharmacopoeia, Cyclophosphamide (CY)) was administered to five 8-week-old BDF1 mice (female) at a dose of 1 mg/animal. Four days after the administration, cells were prepared from the mouse bone marrow by the usual method, and adjusted to the concentration of $2 \times 10^4$ cells/ml with IMDM. The colony assay was then performed in the same manner as in Example 4. Results are shown in FIGS. 6 and 7.

EXAMPLE 6

Figure 8:
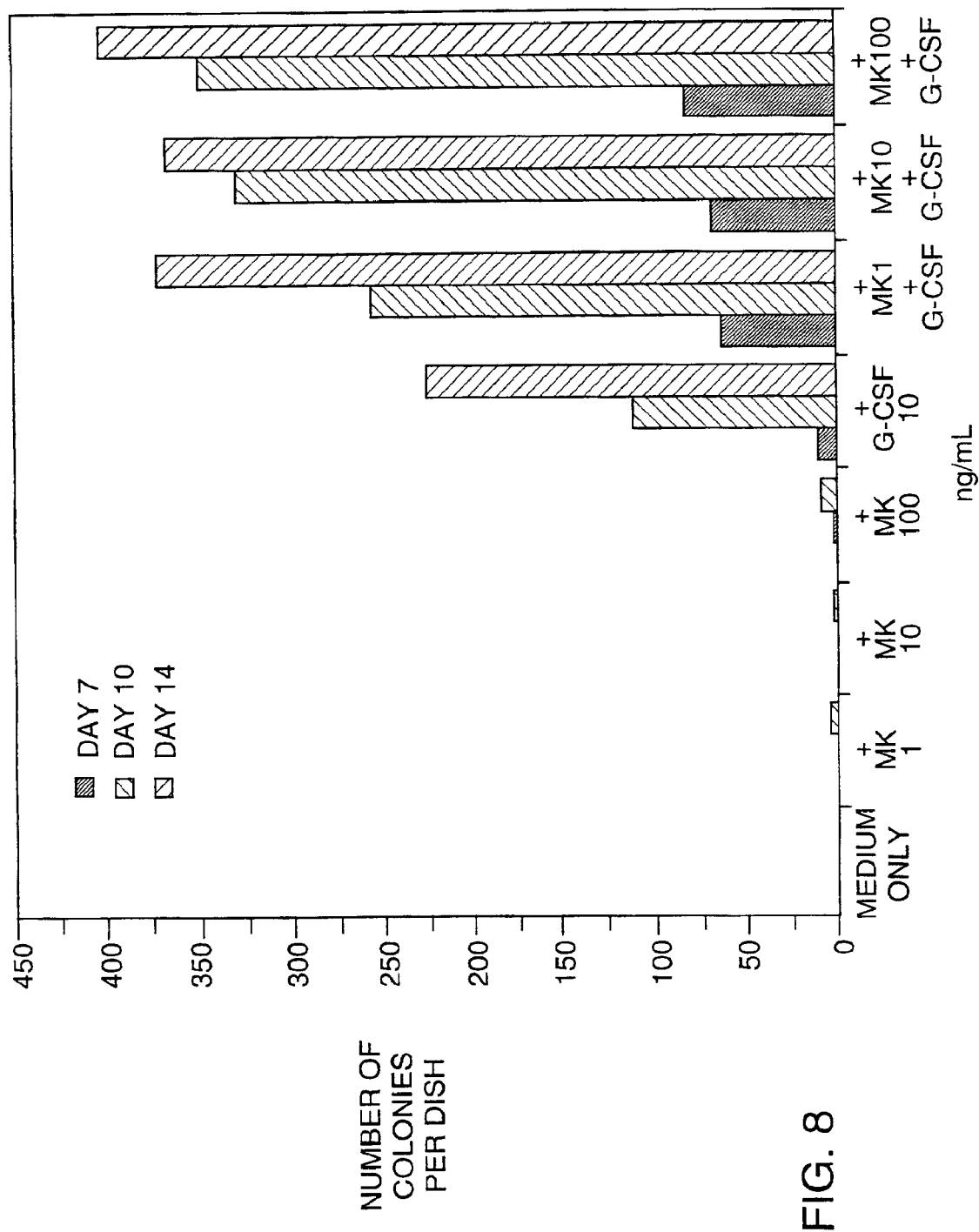
FIG. 8 illustrates effects of MK on colony-forming capability when peripheral blood from a patient with non-Hodgkin's lymphoma was cultured in a methylcellulose medium for the colony assay (MethoCult GF H4230) supplemented with MK, G-CSF, or MK+G-CSF for 14 days.
Figure 9:
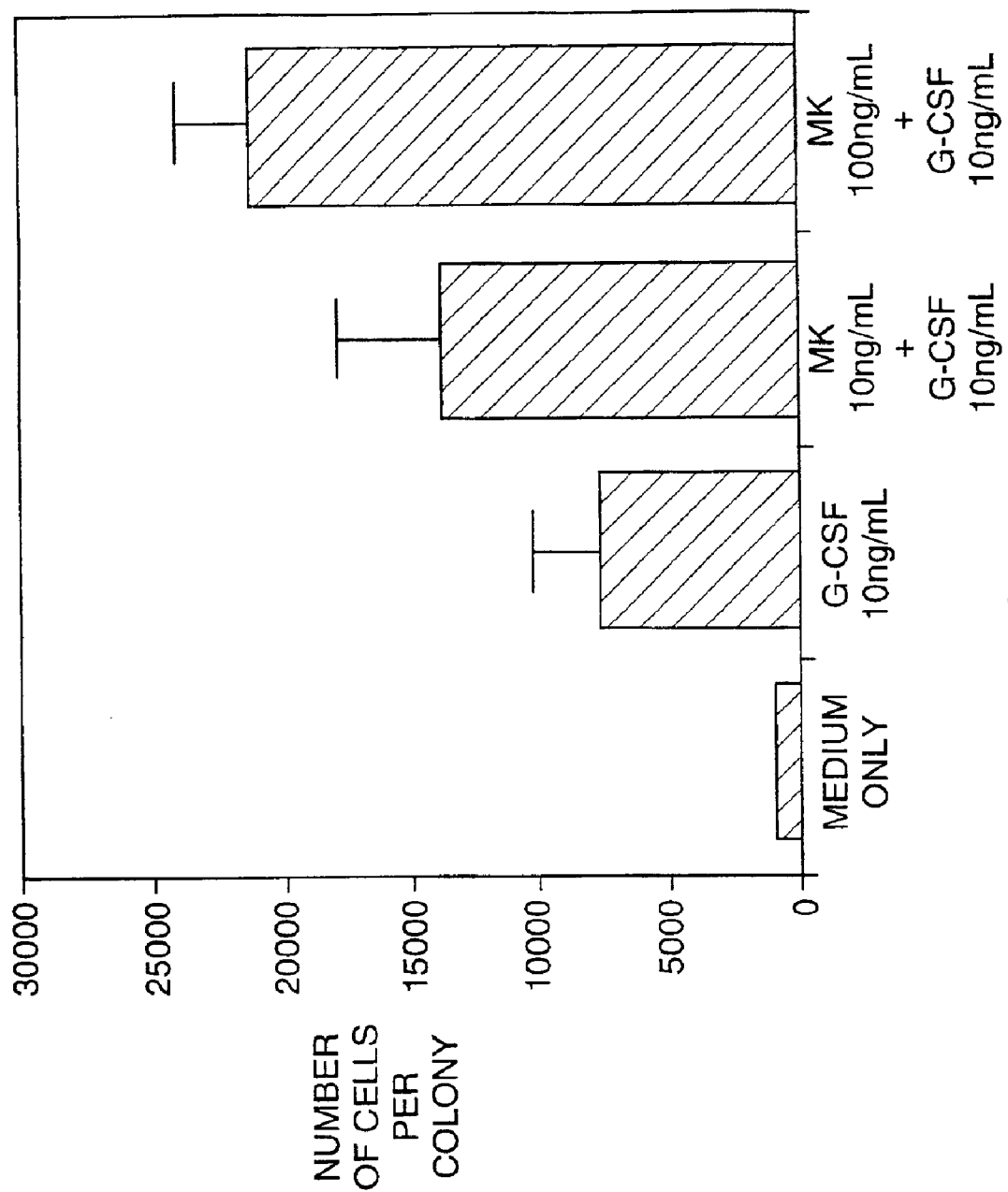
FIG. 9 illustrates the number of colony-constituting cells on the $14^{th}$ day in an experiment similar to that in FIG. 8 where medium alone and that supplemented with G-CSF or MK+CSF was used.

Effects of MK and Other Cytokines on the Colony Formation of Peripheral Blood Mononuclear Cells from a Patient with Non-Hodgkin's Lymphoma The medium used was a methylcellulose medium, MethoCult H4230 (containing a final concentration of 0.9% methylcellulose, 10 to 4 M 2-mercaptoethanol, 2 mM L-glutamine, 30% FBS, and 1% bovine serum albumin; Stem Cell Technologies, Inc.). Results are shown in FIGS. 8 and 9.

EXAMPLE 7

Figure 10:
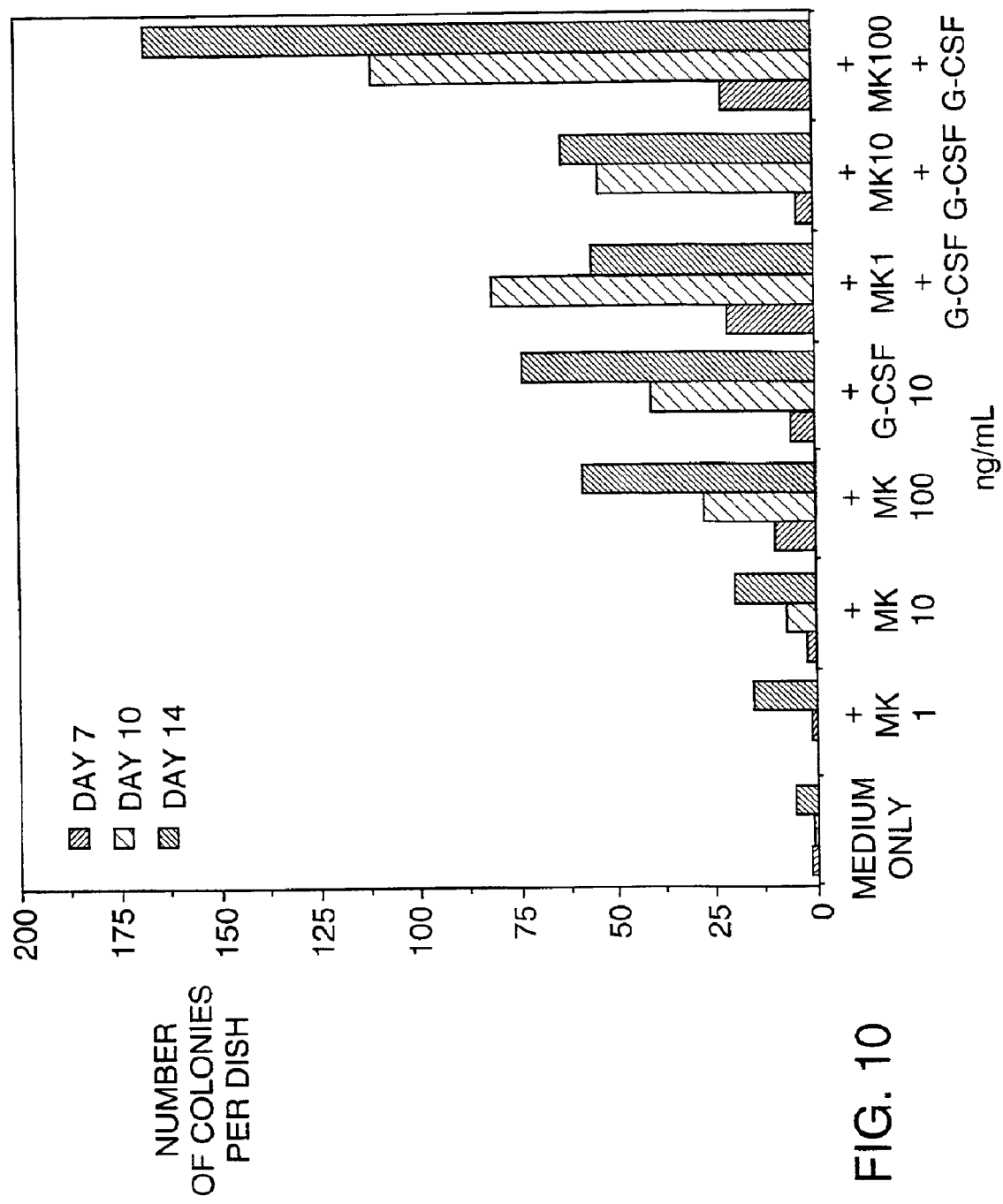
FIG. 10 illustrates effects of MK and G-CSF on colony-forming capability when peripheral blood from a healthy normal individual was cultured in a methylcellulose medium for the colony assay (MethoCult GF H4230) supplemented with MK, G-CSF, or MK+G-CSF.
Figure 11:
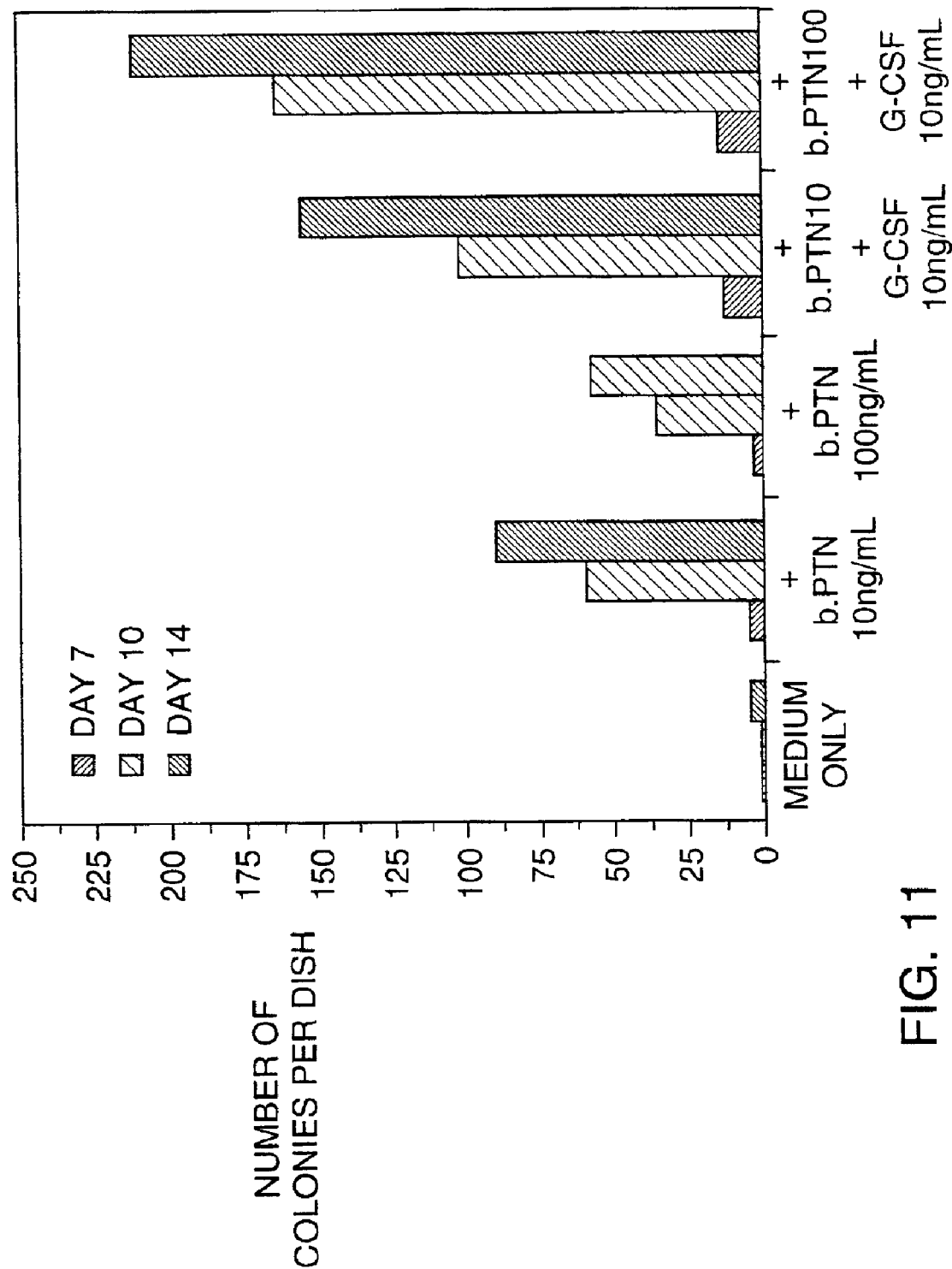
FIG. 11 illustrates results of an experiment similar to that in FIG. 10 where PTN was used in place of MK.
Figure 12:
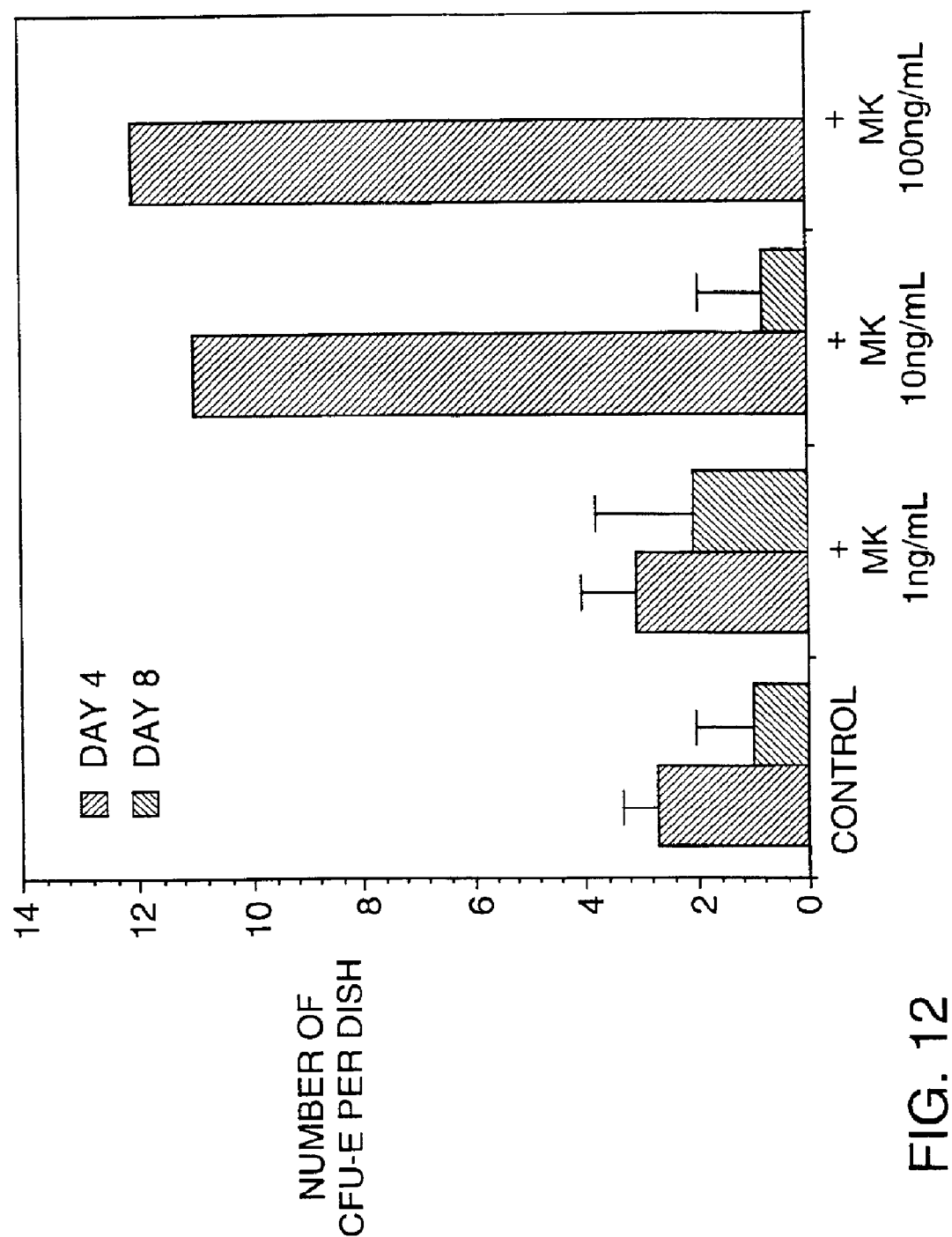
FIG. 12 illustrates effects of MK on CFU-E colony-forming capability when the same human peripheral blood used in the experiment of FIG. 10 was cultured in a medium for the blood stem cell assay containing EPO, IL-3, G-CSF, and SCF supplemented with MK.
Figure 13:
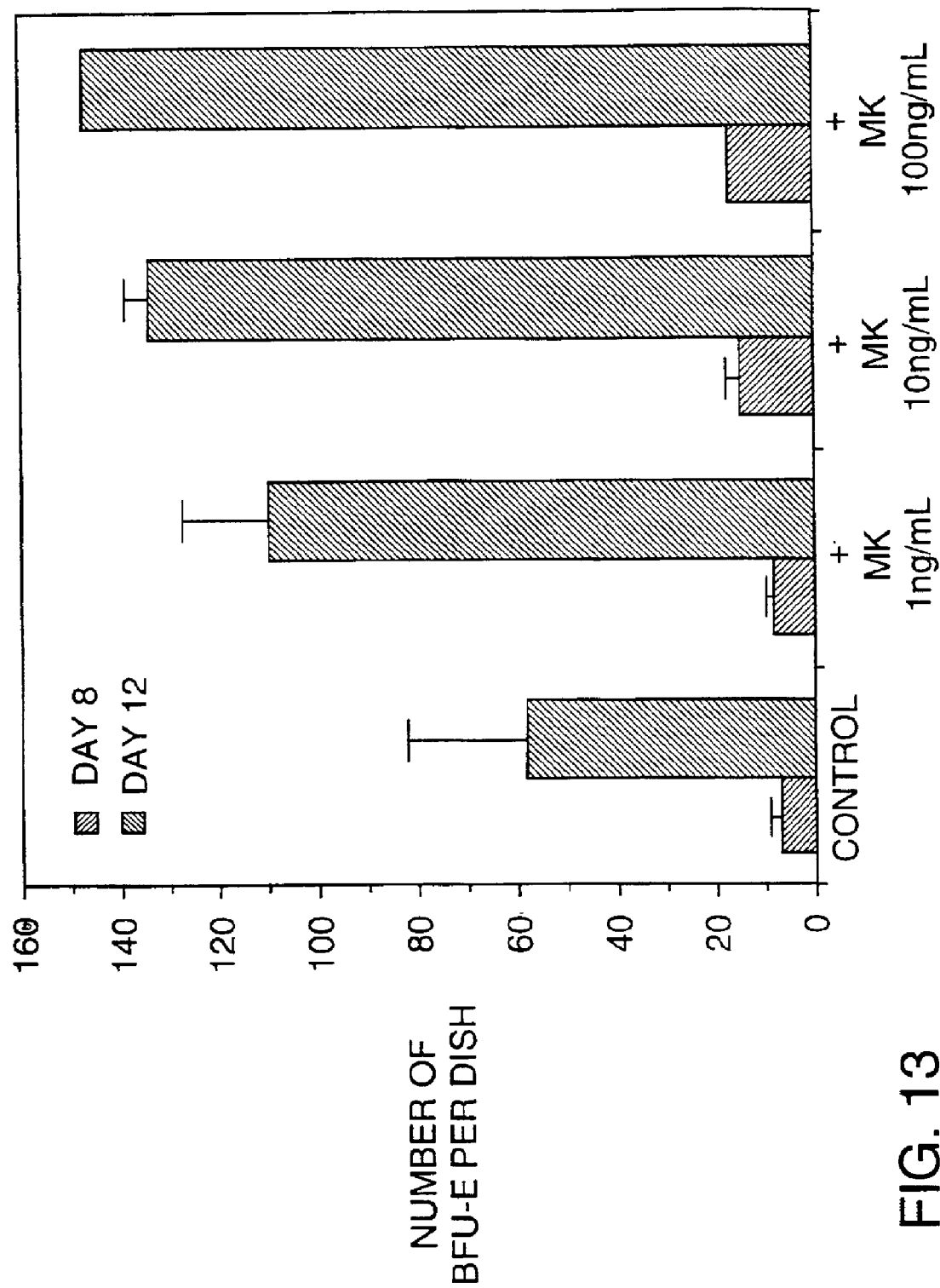
FIG. 13 illustrates effects of MK on the colony-forming capability of BFU-E, which is more undifferentiated than CFU-E, in an experiment similar to that in FIG. 12.
Figure 14:
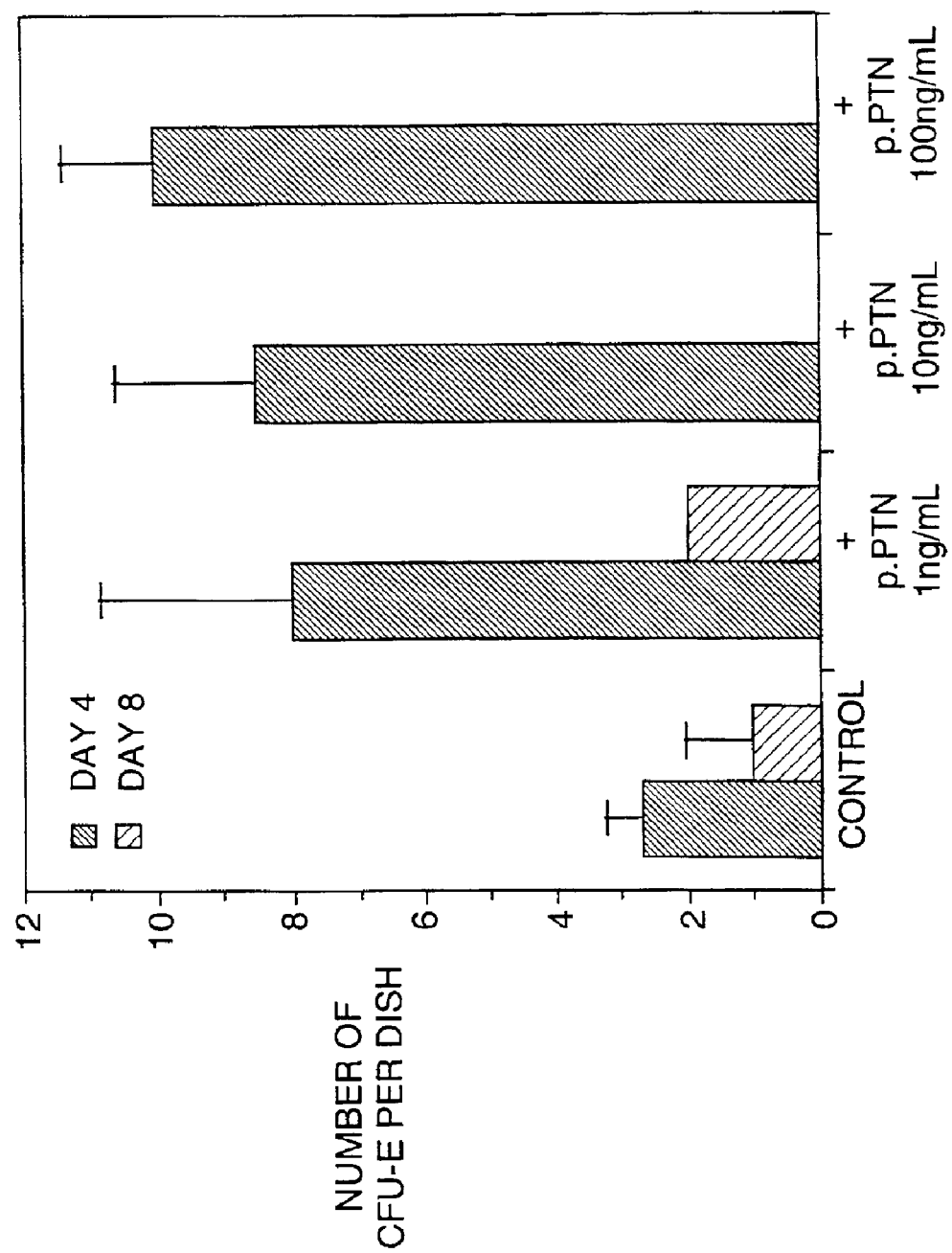
FIG. 14 illustrates effects of PTN on CFU-E colony-forming capability when peripheral blood from the same healthy normal individual used in the experiment of FIG. 10 was cultured in the same medium used in the experiment of FIG. 10 supplemented with PTN in place of MK.
Figure 15:
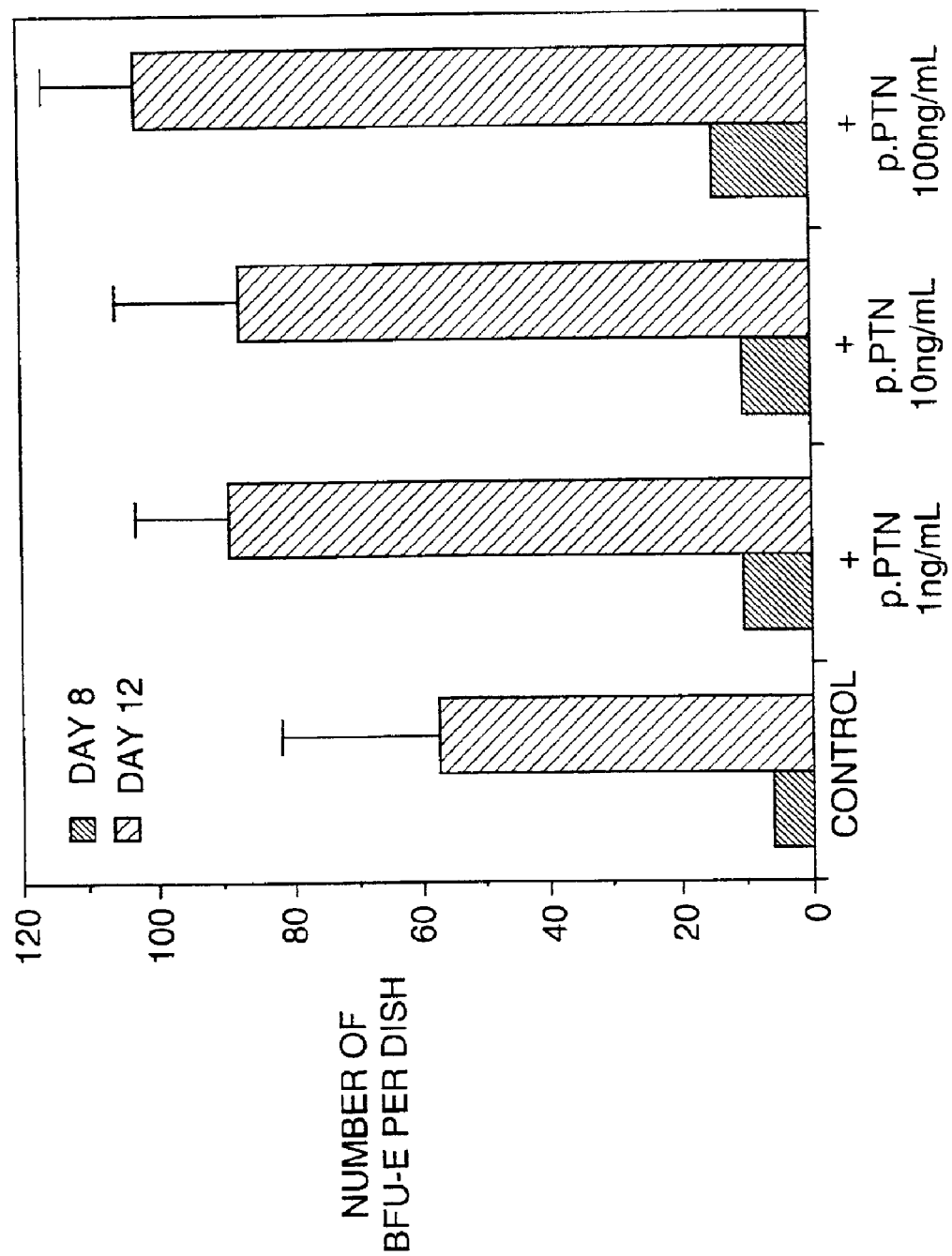
FIG. 15 illustrates effects of PTN on BFU-E colony-forming capability in an experiment similar to that in FIG. 14.

Effects of MK and PTN on the Colony Formation of Peripheral Blood Mononuclear Cells from Healthy Normal Individual The colony assay was carried out using the same medium used in Example 6. Results are shown in FIGS. 10 and 11.

EXAMPLE 8

Effects of MK and PTN on Erythroblast Colony Formation of Peripheral Blood Mononuclear Cells from Healthy Normal Individual.

The colony assay was carried out using a hematopoietic stem cell assay medium (complete type, Kyokuto Seiyaku Kogyo, containing 30% FCS, 1% BSA, 10 to 4 M 2-mercaptoethanol, IMDM, PS solution, 1.2% methylcellulose, 10 ng/ml IL-3, 10 ng/ml G-CSF, 2 U/ml EPO, and 50 ng/ml SCF). Results are shown in FIGS. 12, 13, 14, and 15.

INDUSTRIAL APPLICABILITY

The MK family acts on hematopoietic stem cells and precursor cells of various hemocytes of hematopoietic tissues of mammals to maintain proliferate, and differentiate them. Furthermore, the above-described functions are synergistically or additionally enhanced by the combined use or MK with other cytokines such as SCF, M-CSF, G-CSF, GM-CSF, IL-3, and IL-6. Especially, the MK family exerts remarkable proliferation promoting effects on CFU-Mix, which is very close to multipotential stem cells, under conditions closer to in vivo. The MK family also promotes the proliferation and differentiation of precursor cells of the granulocytes/macrophages and remarkably increase neutrophils in neutropenia in vivo. The pharmaceutical composition of the present invention containing the MK family alone, or containing the MK family in combination with one or more cytokines such as SCF, M-CSF, G-CSF, GM-CSF, IL-3, and IL-6 can be clinically applied, especially, to the ex vivo expansion of stem cells in the transplantation of bone marrow and stem cells derived from the peripheral blood and umbilical cord blood. The MK family is also expected to be used for treating and preventing neutropenia, refractory anemia, and leukemia caused by the cancer chemotherapy. Furthermore, the MK family is expected to be used for the steam cell proliferation for gene therapy targeting hematopoietic stem cells.

What is claimed is:

1. A method for promoting ex vivo expansion of hematopoietic stem cells or hematopoietic progenitor cells, said method comprising culturing hematopoietic stem cells or hematopoietic progenitor cells with a composition comprising: (a) purified midkine (MK) protein or purified pleiotrophin (PTN) protein; and (b) one or more other purified hematopoietic growth factors selected from the group consisting of interleukin-3 (IL-3), interleukin-6 (IL-6), granulocyte colony stimulating-factor (G-CSF), granulocyte-macrophage colony-stimulating factor (GM-CSF), stem cell factor (SCF), and erythropoietin (EPO).

2. A method for promoting ex vivo expansion of hematopoietic stem cells or hematopoietic progenitor cells, said method comprising culturing hematopoietic stem cells or hematopoietic progenitor cells with a composition comprising: (a) purified midkine (MK) protein; and (b) one or more other purified hematopoietic growth factors selected from the group consisting of interleukin-3 (IL-3), interleukin-6 (IL-6), granulocyte colony stimulating-factor (G-CSF), granulocyte-macrophage colony-stimulating factor (GM-CSF), stem cell factor (SCF), and erythropoietin (EPO).

3. The method of claim 1, wherein the hematopoietic stem cells or hematopoietic progenitor cells are obtained from bone narrow, peripheral blood, or umbilical cord blood.

4. The method of claim 1, wherein the hematopoietic stem cells are colony-forming units-mix (CFU-mix).

5. The method of claim 1, wherein the other purified hematopoietic growth factors are IL-3, IL-6, SCF, and EPO.

6. The method of claim 2, wherein the hematopoietic stem cells or hematopoietic progenitor cells are obtained from bone marrow, peripheral blood, or umbilical cord blood.

7. The method of claim 2, wherein the hematopoietic stem cells are colony-farming units-mix (CFU-mix).

8. The method of claim 2, wherein the other purified hematopoietic growth factors are IL-3, IL-6, SCF, and EPO.

* * * * *

UNITED STATES PATENT AND TRADEMARK OFFICE
CERTIFICATE OF CORRECTION

PATENT NO. : 6,939,669 B2
DATED : September 6, 2005
INVENTOR(S) : Makoto Kikuchi et al.

It is certified that error appears in the above-identified patent and that said Letters Patent is hereby corrected as shown below:

Title page,
Item [56], References Cited, FOREIGN PATENT DOCUMENTS,
replace "0473233" with -- 0476233 --.
OTHER PUBLICATIONS, add the following:
-- Bessho, Igaku no Ayumi (Progress in Medicine) 180(13):802-806, 1997. --.

Column 12,
Line 55 after "bone" replace "narrow" with -- marrow --.
Line 63, replace "colony-farming" with -- colony-forming --.

Signed and Sealed this

Sixteenth Day of May, 2006

JON W. DUDAS
*Director of the United States Patent and Trademark Office*